United States Patent
Sun et al.

(10) Patent No.: US 11,393,090 B2
(45) Date of Patent: Jul. 19, 2022

(54) ONLINE ADAPTATION OF NEURAL NETWORKS

(71) Applicant: SHANGHAI UNITED IMAGING INTELLIGENCE CO., LTD., Shanghai (CN)

(72) Inventors: Shanhui Sun, Lexington, MA (US); Hanchao Yu, Champaign, IL (US); Xiao Chen, Lexington, MA (US); Zhang Chen, Brookline, MA (US); Terrence Chen, Lexington, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 76 days.

(21) Appl. No.: 17/039,355

(22) Filed: Sep. 30, 2020

(65) Prior Publication Data
US 2021/0158512 A1    May 27, 2021

Related U.S. Application Data

(60) Provisional application No. 62/941,198, filed on Nov. 27, 2019.

(51) Int. Cl.
*G06K 9/00* (2022.01)
*G06T 7/00* (2017.01)
(Continued)

(52) U.S. Cl.
CPC .......... *G06T 7/0012* (2013.01); *A61B 5/0044* (2013.01); *A61B 5/1128* (2013.01);
(Continued)

(58) Field of Classification Search
CPC ... G06T 7/0012; G06T 3/0093; G06T 7/0014; G06T 7/11; G06T 7/248; G06T 7/55; G06T 7/73; G06T 11/206; G06T 13/80; G06T 19/00; G06T 2200/24; G06T 2207/10016; G06T 2207/20081; G06T 2207/20084; G06T 2207/30048; G06T 2210/41; G06T 2207/10072; G06T 7/12; G06T 7/62;
(Continued)

(56) References Cited

U.S. PATENT DOCUMENTS

2018/0259608 A1*  9/2018  Golden ................. G06N 3/02
2019/0311478 A1* 10/2019  Avendi ................ G06K 9/6289
(Continued)

OTHER PUBLICATIONS

Jaderberg et al., "Spatial Transformer Networks", Feb. 2016, arXiv 1506.02025v3.
(Continued)

*Primary Examiner* — Van D Huynh
(74) *Attorney, Agent, or Firm* — Zhong Law, LLC

(57) ABSTRACT

Described herein are neural network-based systems, methods and instrumentalities associated with imagery data processing. The neural networks may be pre-trained to learn parameters or models for processing the imagery data and upon deployment the neural networks may automatically perform further optimization of the learned parameters or models based on a small set of online data samples. The online optimization may be facilitated via offline meta-learning so that the optimization may be accomplished quickly in a few optimization steps.

20 Claims, 7 Drawing Sheets

(51) Int. Cl.
| | |
|---|---|
| *G06T 7/11* | (2017.01) |
| *G06K 9/62* | (2022.01) |
| *G06N 3/04* | (2006.01) |
| *G16H 50/50* | (2018.01) |
| *G16H 50/30* | (2018.01) |
| *G16H 30/40* | (2018.01) |
| *G06F 3/0485* | (2022.01) |
| *G06T 11/20* | (2006.01) |
| *G06T 13/80* | (2011.01) |
| *G06T 19/00* | (2011.01) |
| *G06T 7/55* | (2017.01) |
| *G06T 7/73* | (2017.01) |
| *G06T 7/246* | (2017.01) |
| *A61B 5/00* | (2006.01) |
| *A61B 5/11* | (2006.01) |
| *G06T 3/00* | (2006.01) |
| *G06N 3/08* | (2006.01) |

(52) U.S. Cl.
CPC .......... *A61B 5/7264* (2013.01); *G06F 3/0485* (2013.01); *G06K 9/6267* (2013.01); *G06N 3/0454* (2013.01); *G06N 3/08* (2013.01); *G06T 3/0093* (2013.01); *G06T 7/0014* (2013.01); *G06T 7/11* (2017.01); *G06T 7/248* (2017.01); *G06T 7/55* (2017.01); *G06T 7/73* (2017.01); *G06T 11/206* (2013.01); *G06T 13/80* (2013.01); *G06T 19/00* (2013.01); *G16H 30/40* (2018.01); *G16H 50/30* (2018.01); *G16H 50/50* (2018.01); *G06T 2200/24* (2013.01); *G06T 2207/10016* (2013.01); *G06T 2207/20081* (2013.01); *G06T 2207/20084* (2013.01); *G06T 2207/30048* (2013.01); *G06T 2210/41* (2013.01)

(58) Field of Classification Search
CPC ... A61B 5/0044; A61B 5/1128; A61B 5/7264; G06F 3/0485; G06K 9/6267; G06K 9/6271; G06N 3/0454; G06N 3/08; G06N 3/0445; G06N 3/084; G16H 30/40; G16H 50/30; G16H 50/50; G16H 50/20; G06V 2201/03; G06V 10/454; G06V 10/82
USPC ........................................................ 382/128
See application file for complete search history.

(56) References Cited

U.S. PATENT DOCUMENTS

| | | | |
|---|---|---|---|
| 2019/0365265 A1* | 12/2019 | Grouchy | G06T 11/008 |
| 2020/0051274 A1* | 2/2020 | Siemionow | G06T 7/62 |
| 2020/0219262 A1* | 7/2020 | Hsiao | G06K 9/6268 |
| 2021/0012885 A1* | 1/2021 | Arafati | G06N 3/0454 |
| 2021/0150693 A1* | 5/2021 | Fornwalt | A61B 8/5223 |
| 2021/0287367 A1* | 9/2021 | Meyer | G06T 7/62 |

OTHER PUBLICATIONS

Qin et al., "Joint Learning of Motion Estimation and Segmentation for Cardiac MR Image Sequences", Jun. 2018, arXiv:1806.04066v1.
Finn et al., "Model-Agnostic Meta-Learning for Fast Adaptation of Deep Networks", Jul. 2017, arXiv:1703.03400v3.

* cited by examiner

ONLINE ADAPTATION OF NEURAL NETWORKS

CROSS-REFERENCE TO RELATED APPLICATIONS

This application claims the benefit of Provisional U.S. Patent Application No. 62/941,198, filed Nov. 27, 2019, the disclosure of which is incorporated herein by reference in its entirety.

BACKGROUND

In recent years, deep learning-based image processing techniques have been increasingly employed to improve the quality of various types of services including healthcare services. For instance, artificial neural networks having machine learning capabilities may be trained to learn a prediction model for detecting the differences between adjacent cardiac magnetic resonance (CMR) images and estimate the motion of the heart based on the detected differences. The estimation may then be used to evaluate the anatomy and/or function of the heart, e.g., by calculating subject-specific muscular strains of the myocardium based on the estimation. While these learning-based image processing techniques have shown great promises in improving the accuracy and efficiency of image or video processing, they often suffer dramatic performance drop at deployment. One of the reasons for the performance drop is that it is extremely difficult, if not impossible, to collect data that realistically represent the distribution of the subject matter (e.g., cardiac motion) in the general population. As such, data used to train a neural network often mismatch the data to be processed at an interference or testing time (e.g., post deployment).

Accordingly, it is highly desirable for a pre-trained neural network system to have the ability to perform adaptive online learning so that the neural network system may adjust the model parameters acquired via pre-training based on data received at interference or testing time to increase the robustness of the prediction model. Since the adaptive learning will be performed while the neural network system is online, it is also desirable for such a system to have the ability to complete the online learning in a quick and efficient manner (e.g., using only a small number of samples or via a small number of steps).

SUMMARY

Described herein are neural network-based systems, methods and instrumentalities associated with imagery data processing such as motion tracking and/or image registration. A system as described herein may comprise at least one processor configured to implement one or more artificial neural networks (e.g., an encoder network and/or a decoder network) having predetermined parameters for processing images or videos of an anatomical structure (e.g., a myocardium). Upon bringing the one or more artificial neural networks online to process the images or videos, the at least one processor may (e.g., while the one or more artificial neural networks are online) perform online adjustments to the predetermined parameters of the one or more artificial neural networks based on a first set of online images of the anatomical structure. The online adjustments may be performed, for example, by determining a loss associated with processing the first set of online images using the predetermined parameters and adjusting the predetermined parameters based on a gradient descent associated with the loss (e.g., by backpropagating the gradient descent through the one or more artificial neural networks). Once the predetermined parameters are adjusted (e.g., optimized based on the first set of online images), the at least one processor may process a second set of online images of the anatomical structure using the adjusted parameters of the one or more artificial neural networks.

The predetermined parameters of the one or more artificial neural networks may be acquired via offline meta-learning that facilitates the online adjustments of the parameters. The meta-learning may be performed using respective instances of the one or more artificial neural networks configured with baseline parameters and a training set that comprises multiple training videos. For each of the multiple training videos, a respective copy of the baseline parameters may be obtained. A first set of training images (e.g., K pairs of images where K may be equal to one for image registration tasks and greater than one for motion tracking tasks) may be selected from each of the training videos and a respective first loss associated with processing the first set of training images using the respective copy of the baseline parameters may be determined. The respective copy of the baseline parameters may then be optimized based on a gradient descent associated with the first loss. Responsive to optimizing the respective copy of the baseline parameters associated with each of the training videos, a second set of training images may be selected from the training video and a second loss associated with processing the second set of training images using the optimized copy of the baseline parameters may be determined. An average of the respective second losses associated with processing the respective second sets of training images of the multiple training videos may be determined, and the baseline parameters may be updated based on a gradient descent associated with the average loss. Alternatively, responsive to optimizing the respective copy of the baseline parameters associated with each of the training videos and determining the second loss associated with processing the second set of training images using the optimized copy of the baseline parameters, a gradient descent associated with the second loss may be determined and the baseline parameters may be updated based on an average of the respective gradient descents associated with processing the respective second sets of images. In either case, the first and second losses may be determined based on a loss function and the baseline parameters may be updated based on a first order approximation of the loss function.

The baseline parameters used during the meta-learning may be derived based on a first training set characterized by a first distribution and the multiple training videos used for the meta-learning may be derived from a second training set characterized by a second distribution that mismatches the first distribution.

BRIEF DESCRIPTION OF THE DRAWINGS

A more detailed understanding of the examples disclosed herein may be obtained from the following description, given by way of example in conjunction with the accompanying drawing.

DETAILED DESCRIPTION

The present disclosure is illustrated by way of example, and not by way of limitation, in the figures of the accompanying drawings.

Figure 1A:
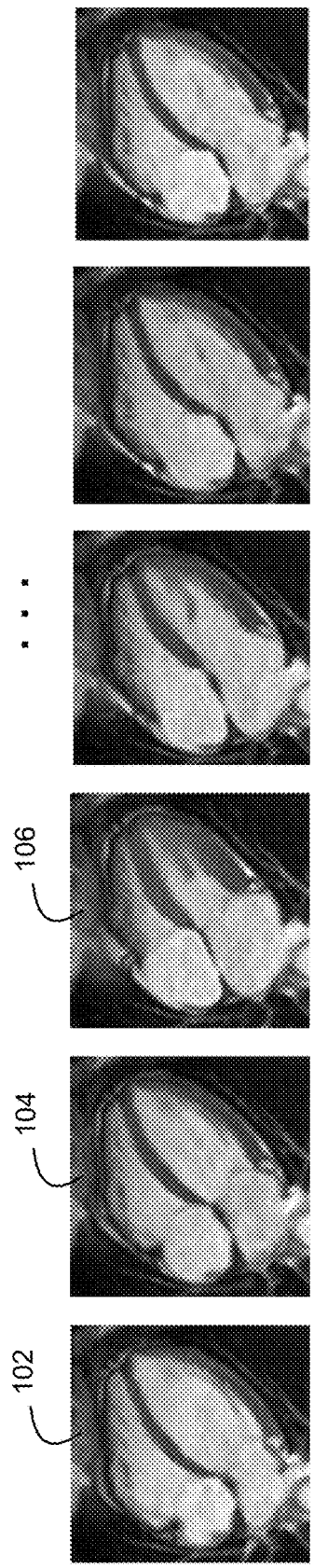
FIG. 1A and FIG. 1B are block diagrams illustrating example application areas in which an image processing system as described herein may be deployed.
Figure 1B:
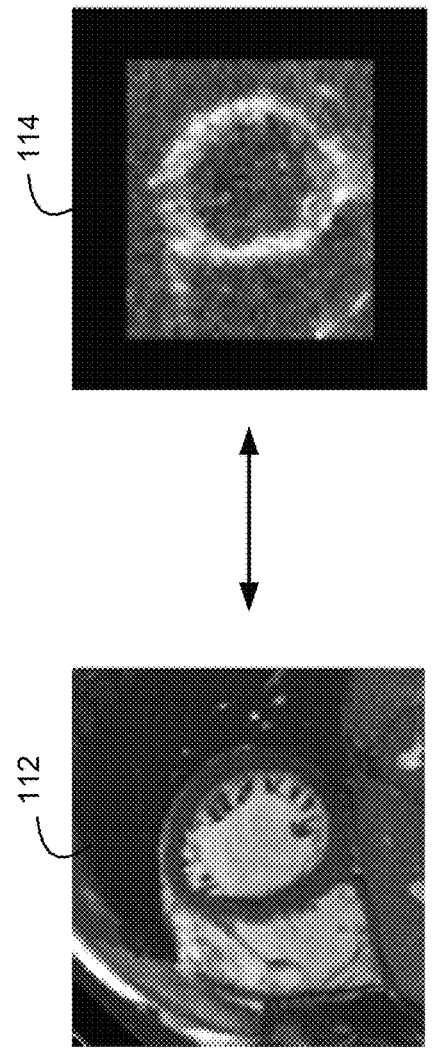

FIGS. 1A and 1B are block diagrams illustrating examples of motion tracking and image registration that may be performed by a system or apparatus described herein. The examples will be described in the context of cardiac magnetic resonance imaging (MRI), but it should be noted that the use of the systems, methods and instrumentalities disclosed herein is not limited to medical images or certain types of imaging modalities. Rather, the disclosed systems, methods and instrumentalities may be applicable to a variety of image processing tasks including, for example, estimating optical flows based on camera captured videos.

FIG. 1A shows an example of cardiac motion tracking (e.g., estimation) based on an MRI video of the human heart such as a cine MM that may comprise a plurality of images of the heart recorded at different points in time (e.g., sequential points in time along a time axis t). The video may depict one or more cycles of cardiac contraction and relaxation. As such, starting from a first image frame 102 of the video, a medical image processing system or apparatus as described herein may estimate the motion of the heart (e.g., the myocardium) between the first image frame 102 and a second image frame 104 by comparing visual features of the two image frames (e.g., closed-boundary regions, edges, contours, line intersections, corners, etc.) and identifying changes that have occurred in the images between the time the first image frame 102 was captured and the time the second image frame 104 was captured. The image processing system may then use the second image frame 104 as a new reference frame and repeat the estimation process for the image frame 104, a third image frame 106, and the remaining frames to obtain motion information for one or more full cardiac cycles.

FIG. 1B shows an example of cardiac image registration that may involve aligning and/or overlaying two or more images (e.g., a reference image 112 and a sensed image 114) of the same area taken at different times, from different viewpoints, by different image sensors, etc. Image registration is an important part of many medical applications in which images from various sources may be combined to obtain a complete assessment of a patient's medical conditions (e.g., for monitoring tumor growth, treatment verification, comparison of the patient's data with anatomical atlases, etc.). The image processing system described herein may be trained to perform the image registration task for images 112 and 114 by detecting salient and distinctive objects (e.g., closed-boundary regions, edges, contours, line intersections, corners, etc.) in the images, establishing a correspondence (e.g., via a displacement field or a transformation matrix) between the objects detected in the reference image 112 and those detected in the sensed image 114, estimating a transform model (e.g., one or more mapping functions) for aligning the sensed image 114 with the reference image 112 based on the established correspondence, and then resampling and/or transforming (e.g., via linear interpolation) the sensed image 114 to be aligned with the reference image 112 (or vice versa) using the transform model.

In the motion tracking and image registration examples shown in FIGS. 1A and 1B, the image processing system may be configured to determine a motion field (e.g., in the form of a vector field, a grid of vectors, a vector-value function or a combination thereof) that represents the displacement of visual features from a first image of an anatomical structure to a second image of the anatomical structure and indicates the motion (e.g., translation, rotation, scaling, etc.) of the anatomical structure from the first image to the second image. When respective motion fields between multiple pairs of such images are obtained (e.g., as shown in FIG. 1A), the image processing system may be able to track the motion of the anatomical structure through the multiple images. Similarly, based on a motion field between one pair of images (e.g., as shown in FIG. 1B), the image processing system may be able to perform motion registration for the pair of images.

Figure 2:
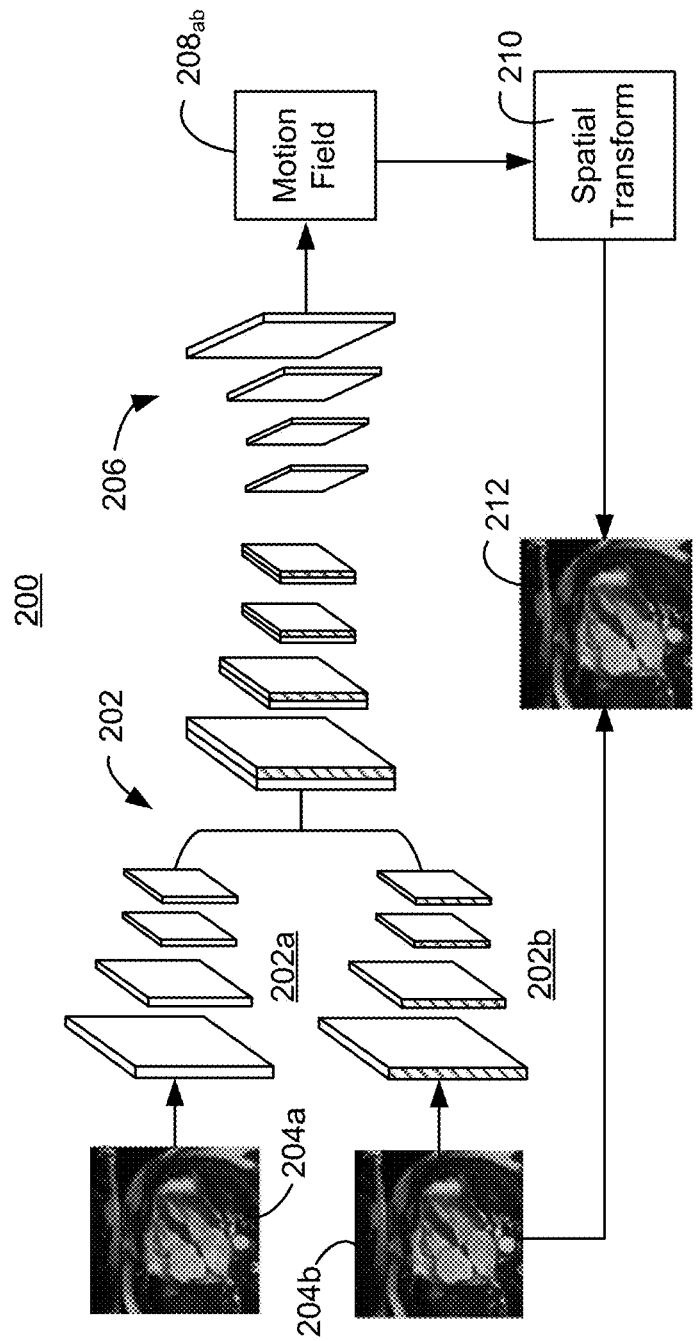
FIG. 2 is a block diagram illustrating an example of estimating a motion field using the image process system described herein.

FIG. 2 is a block diagram illustrating an example of estimating a motion field using an image processing system 200 as described herein. The example will be described with reference to certain neural network structure or components, but it should be noted that the techniques disclosed herein may also be implemented using other types of neural network structure or components. Consequently, the structure or components shown or described herein are only illustrative, and not restrictive.

As shown in FIG. 2, the image processing system 200 may include a feature tracking neural network 202 configured to receive a pair of input images 204a and 204b of an anatomical structure such as a myocardium and extract visual features from the images. The images may be parts of a cardiac cine movie, e.g., similar to that described in association with FIG. 1. The feature tracking networking 202 may include twin subnetworks 202a and 202b, which may be arranged in a Siamese configuration to process the input images 204a and 204b in tandem. The subnetworks 202a and 202b may be twin neural networks having similar operating parameters or weights (e.g., the weights of the subnetworks 202a and 202b may be the same). Each of the subnetwork 202a and 202b may comprise an artificial neural network such as a convolutional neural network (CNN) or a fully convolutional neural network (FCN) and the artificial neural network may in turn include a plurality of layers such as one or more convolutional layers, one or more pooling layers, and/or one or more fully connected layers. The convolutional layers of the neural network may include a plurality of convolution kernels or filters configured to extract specific features from the input image 204a or 204b via one or more convolution operations. The convolution operations may be followed by batch normalization and/or non-linear activation, and the features extracted by the convolutional layers (e.g., in the form of one or more feature maps) may be down-sampled through the one or more pooling layers (e.g., using a 2×2 window and a stride of 2) to reduce the redundancy and/or dimension of the features (e.g., by a factor of 2). As a result of the convolution and/or down-sampling operations, respective feature representations (e.g., latent space representations) of the input images 204a and 204b may be obtained, for example, in the form of twin feature maps or feature vectors, and/or at multiple levels of scale and abstraction.

The feature maps or feature vectors associated with the input images 204a and 204b may be compared or matched (e.g., at a patch level and/or via a correlation layer) to determine the differences or changes (e.g., displacement) between the two input images and further estimate a motion (e.g., flow) of the anatomical structure based on the determined differences or changes (e.g., as indicated by a similarity metric or a score map). The image processing system 200 may include a motion tracking neural network 206 (e.g., a multi-scale decoder network) configured to perform such an estimation task. The motion tracking network 206 may comprise one or more CNNs or FCNs and each of the CNNs or FCNs may include a plurality of layers such as a plurality of convolutional layers (e.g., transposed convolutional layers) and/or un-pooling layers. Through these layers, the motion tracking network 206 may perform a series of up-sampling and/or transposed convolution operations on the feature maps or feature vectors produced by the feature extraction network 202 (e.g., at multiple levels of scale and abstraction) to decode the features and restore them to the original image size or resolution. For instance, the motion tracking network 206 may up-sample the feature representations produced by the feature extraction network 202 based on pooled indices stored by the feature extraction network 202. The motion tracking network 206 may then process the up-sampled representations through one or more transposed convolution operations (e.g., using 3×3 transposed convolutional kernels with a stride of 2) and/or one or more batch normalization operations to obtain one or more dense feature maps (e.g., up-scaled by a factor of 2). Based on the dense feature maps, the motion tracking network 206 may predict a motion field 208ab (e.g., in the form of a vector field, a grid of vectors, a vector-value function or a combination thereof) that represents the displacement of visual features from the input image 204a to the input image 204b, thereby indicating the motion of the anatomical structure from image 204a to image 204b.

The image processing system 200 shown in FIG. 2 (e.g., the feature extraction network 202 and/or the motion tracking network 206) may learn the parameters (e.g., weights) associated with predicting the motion field 208ab through individualized as well as end-to-end training. The training may be performed, for example, using a train set that comprises multiple images or videos of the target anatomical structure. Since annotating motion fields for an anatomical structure is a substantially intractable task, the training of the image processing system 200 may be conducted in an unsupervised or self-supervised manner. For instance, the image processing system 200 may include a spatial transformation network 210 (e.g., a differentiable spatial transformation network) configured to generate a warped image 212 based on the input image 204a and the predicted motion field 208ab. The training of the image processing system 200 may then be performed with an objective of minimizing the difference between the warped image 212 and the input image 204b, which serves as a reference image in the training process.

The spatial transformation network 210 may include an input layer, one or more hidden layers (e.g., convolutional layers), and/or an output layer. In operation, the spatial transformation network 210 may take the input image 204a (e.g., one or more feature maps of the input image 204a generated by the feature extraction network 202) and/or the motion field 208ab, obtain a plurality of transformation parameters based on the motion field 208ab, and create a sampling grid including a set of points from which the input image 204a may be sampled to generate the transformed or warped image 212. The input image 204a and the sampling grid may then be provided to a sampler of the spatial transformation network 210 to produce an output image (e.g., the warped image 212) by sampling from the input image 204a at the grid points.

The difference between the warped image 212 and the reference image 204b may be represented by a reconstruction loss function $L_{recon}$, which may be based on, for example, mean squared errors (MSE) between the warped image 212 and the reference image 204b. In addition to the reconstruction loss function $L_{recon}$, the training of the image processing system 200 may also consider a motion field smoothness loss $L_{smooth}$ (e.g., to prevent predictions that result in unrealistic, abrupt motion changes between adjacent image frames) and/or a bidirectional flow consistency loss $L_{con}$ that ensures that respective motion fields predicted in a forward direction (e.g., using the input image 204a as the source image and the input image 204b as the target image) and a backward direction (e.g., using the input image 204b as the source image and the input image 204a as the target image) are consistent with each other (e.g., having a difference less than a predetermined threshold). A total loss $L_{total}$ may then be derived (e.g., as shown in Equation (1) below) and used to guide the training of the image processing system 200:

$$L_{total}=L_{recon}+\alpha_s L_{smooth}+\beta_c L_{con} \qquad (1)$$

where $\alpha_s$ and $\beta_c$ are balance parameters that may be adjusted during the training to improve the quality of the training.

While the image processing system 200 may learn a baseline model for predicting a motion field associated with an anatomical structure via the training process described above, the performance of the model may suffer at a testing or inference time, for example, when the image processing system 200 and the neural network(s) comprised thereof are brought online (e.g., post training and/or deployed) to process medical imaging in real time. Numerous factors may contribute to the performance drop, including, e.g., mismatch between the distribution of data used for training the image processing system 200 and the distribution of data to be processed post deployment (e.g., due to the long-tail problem often present in medical imaging data). Accordingly, the image processing system 200 described herein may be configured with online learning capabilities so that upon being deployed to process real medical imagery data, the system may further optimize its parameters (e.g., adapt the prediction model learned through pretraining) in accordance with the characteristics of the data to be processed.

Figure 3:
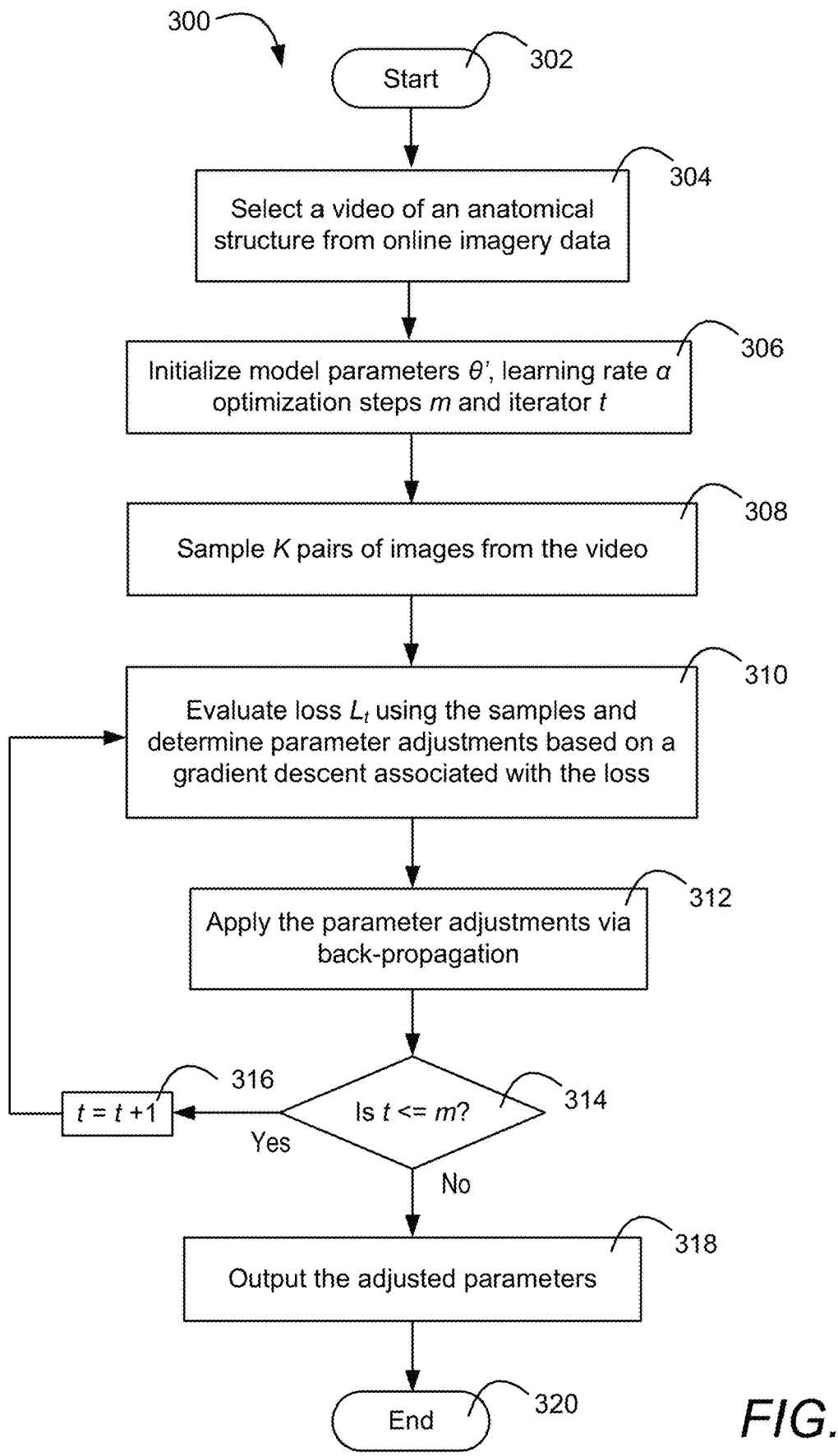
FIG. 3 is a flow diagram illustrating an example of adaptive online learning in accordance with one or more embodiments described herein.

FIG. 3 illustrates an example online optimization process 300 that may be implemented by an image processing system described herein (e.g., the image processing system 200 in FIG. 2) to adjust one or more predetermined parameters of the image processing system. The online optimization process 300 may be started at 302, for example, by an online optimizer (e.g., a gradient descent-based optimizer) of the image processing system and responsive to one or more neural networks of the image processing system being brought online to process medical imagery data associated with an anatomical structure (e.g., cardiac cine videos depicting a left ventricle and/or a myocardium). At 304 (e.g., before starting to process the medical imagery data), the online optimizer may select (e.g., randomly) a video from the online data for evaluating and/or adjusting the predetermined parameters (e.g., weights) of the neural networks. At 306, the online optimizer may derive an initial version of the parameters to be optimized (denoted as $\theta_t'$), for example, as a copy of the predetermined parameters $\theta$ (e.g., $\theta_t' \leftarrow \theta$). The online optimizer may also initialize other parameters associated with the optimization process including, e.g., a learning rate $\alpha$ that may be predetermined as a hyperparameter or meta-learned, the number of online optimization steps m to be completed, an iterator t (initially set to 1) for the optimization steps, etc., at 306.

At 308, the online optimizer may sample K pairs of images from the selected video to form an optimization dataset $D_t = \{a_t^{(j)}, b_t^{(j)}\}$, where j=1 . . . K (e.g., K may be greater than 1 for a motion tracking task and equal to 1 for an image registration task) and each pair of sampled images may include a source image and a reference image (e.g., similar to the images 204a and 204b in FIG. 2) that may be used to predict a respective motion field. At 310, the online optimizer may evaluate (e.g., determine) a loss associated with processing the optimization dataset $D_t$ using the current network parameters $\theta_t'$. The online optimizer may determine the loss, for example, based on the loss function defined in Equation (1) above. Responsive to determining the loss, the online optimizer may further determine adjustments that should be made to the current network parameters $\theta_t'$ in order to reduce or minimize the loss. For instance, the online optimizer may determine the adjustments based on a gradient descent (e.g., a stochastic gradient descent), $\nabla_{\theta_t'} \cdot L_t(f_{\theta_t'})$, of the loss function of Equation (1), where $L_t(f_{\theta_t'})$ may represent the loss associated with processing the optimization dataset $D_t$ using the current network parameters $\theta_t'$. Once the adjustments are determined, the online optimizer may apply the adjustments at 312, for example, by backpropagating the adjustments through the neural networks based on the learning rate $\alpha$, as illustrated below:

$$\theta_t' \leftarrow \theta_t' - \alpha \nabla_{\theta_t'} \cdot L^t(f_{\theta_t'}) \quad (2)$$

At 314, the online optimizer may determine whether additional optimization steps need to be performed, for example, by comparing the value of t with m. If the determination is that t is equal to or less than m, the online optimizer may increment the value of t (e.g., by one) at 316 and repeat the operations of 310-314. If the determination at 314 is that t is greater than m, the online optimizer may output and/or store the adjusted parameters $\theta_t'$ at 318 and exit the online optimization process 300 at 320.

Figure 4:
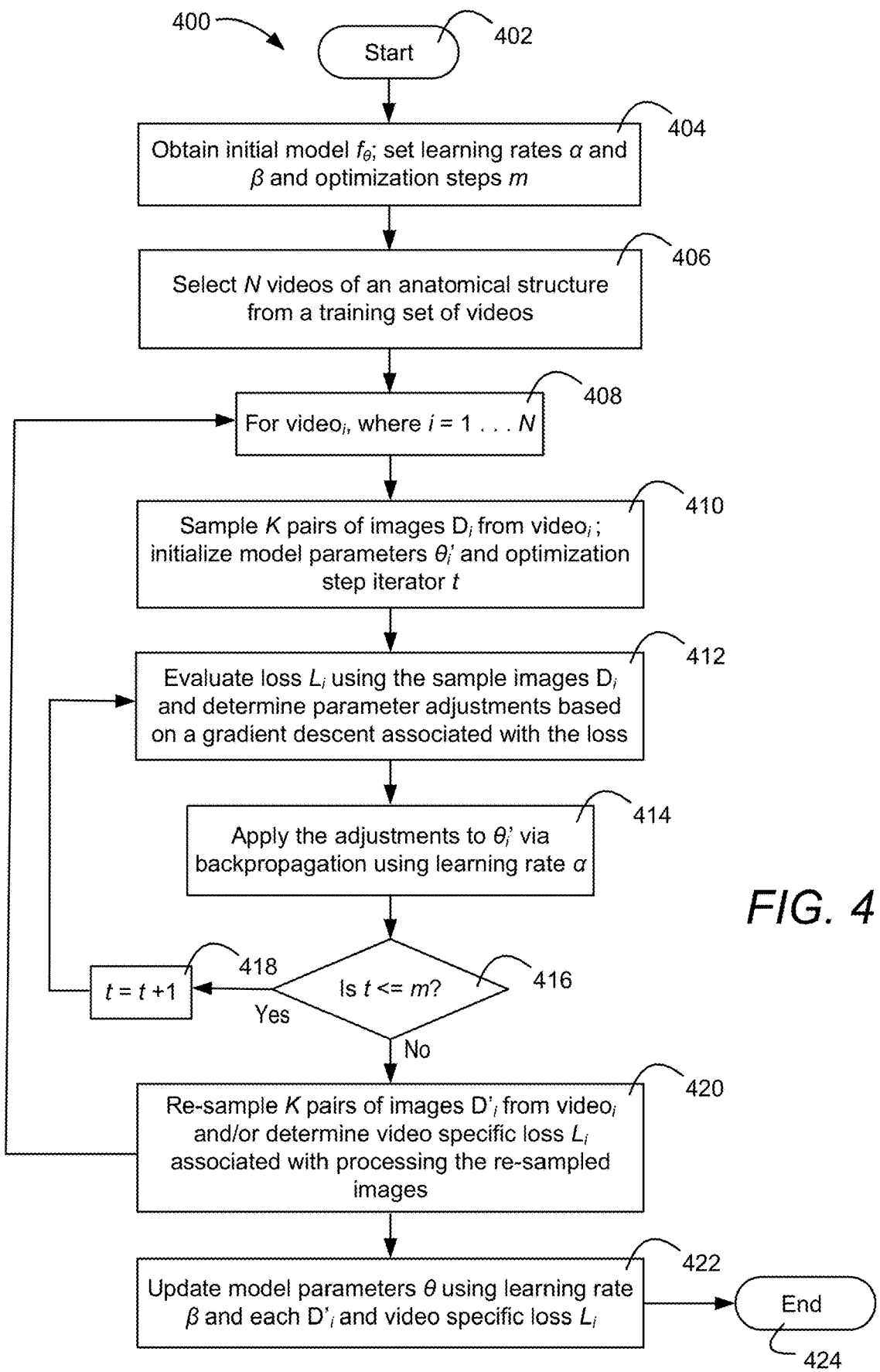
FIG. 4 is a flow diagram illustrating an example of meta-learning in accordance with one or more embodiments described herein.

Since the optimization operation described above is performed online, it may be desirable to complete the operation with just a small number of steps and/or a small number of online samples so that optimization of the system may be accomplished quickly. The image processing system described herein may be provided with the ability to perform the online optimization in this desired manner via meta-learning. FIG. 4 illustrates an example meta-learning process 400 that may be executed by the image processing system to train the online optimizer to quickly adapt or adjust a pre-learned model based on a small set of samples of online data. The example will be described with reference to the use of a plurality of training videos. It should be noted, however, that the meta-learning may also be conducted using a training set comprising images (e.g. paired images) and/or other forms of data, for example, for an image registration task.

The meta-learning process 400 may be started at 402, for example, during offline training of the image processing system (e.g., after the image processing system has learned a baseline mode $f_\theta$ for motion tracking or image registration.

At 404, the image processing system may obtain the baseline parameters $\theta$ of the pre-learned model $f_\theta$ and initialize one or more other parameters associated with the meta-learning process 400, including, e.g., learning rates $\alpha$ and $\beta$ (e.g., predetermined as a hyperparameter or meta-learned) to be applied in the meta-learning process (e.g., $\alpha$ and $\beta$ may be the same or may be different), the number of optimization steps m to be executed during the meta-learning process, etc. At 406, the image processing system may select a plurality (e.g., N) of videos of an anatomical structure from a training set. The distribution of the N videos may match that of the videos used to pre-train the image processing system (e.g., to acquire the predetermined parameters $\theta$) or the distribution of the N videos may mismatch the distribution of the pre-training videos (e.g., the N videos may be from a different training set than the pre-training set).

At 408, the image processing system may start processing the N videos. For each of the videos i, the image processing system may sample K pairs of images from the video at 410 to form a dataset $D_i = \{a_i^{(j)}, b_i^{(j)}\}$, where j=1 . . . K (e.g., K may be greater than 1 for a motion tracking task and equal to 1 for an image registration task) and each pair of sampled images may include a source image and a reference image (e.g., similar to the images 204a and 204b in FIG. 2) that may be used to predict a respective motion field. At 410, the image processing system may also initialize an optimization step iterator t (e.g., set to 1) and derive an initial version of the parameters to be adjusted, $\theta_i'$, by copying from the predetermined baseline parameters $\theta$. At 412, the image processing system may evaluate (e.g., determine) a loss associated with processing the dataset using the current copy of the network parameters, $\theta_i'$. The image processing system may determine the loss, for example, based on the loss function defined in Equation (1) above. Responsive to determining the loss, the image processing system may further determine adjustments that should be made to the current network parameters $\theta_i'$ in order to reduce or minimize the loss. For instance, the image processing system may determine the adjustments based on a gradient descent (e.g., a stochastic gradient descent), $\nabla_{\theta_i'}(f_{\theta_i'})$, of the loss function of Equation (1), where $L_i(f_{\theta_i'})$ may represent the loss associated with processing the optimization dataset $D_i$ using the current network parameters $\theta_i'$. Once the adjustments are determined, the online optimizer may apply the adjustments at 414, for example, by backpropagating the adjustments through the neural networks of the image processing system based on the learning rate $\alpha$, as illustrated below:

$$\theta_i' \leftarrow \theta_i' - \alpha \nabla_{\theta_i'} \cdot L_i(f_{\theta_i'}) \quad (3)$$

At 416, the image processing system may determine whether additional optimization steps need to be performed, for example, by comparing the value of t with m. If the determination is that t is equal to or less than m, the image processing system may increment the value of t (e.g., by one) at 418 and repeat the operations of 412-416. If the determination at 416 is that t is greater than m, the image processing system may proceed to 420 where the image processing system may re-sample (and/or store) K pairs of images $D_i'$ from video i and/or determine (e.g., re-compute) the loss associated with processing the re-sampled images using the optimized parameters $\theta_i'$.

From 420, the image processing system may return to 408 and repeat the operations at 410-420 until all N videos are processed. The image processing system may then proceed to 422 to adjust the predetermined parameters $\theta$ based on the learning rate $\beta$ and each $D_i'$ (e.g., re-sampled K pairs of images from video i), before exiting the meta-learning process 400 at 424. For instance, the image processing system may, at 422, adjust the predetermined parameters θ based on recalculated loss $L_i(f_{\theta_i'})$ associated with processing the re-sampled K pairs of images from each video using the optimized parameters $\theta_i'$, determining an average of the respective losses $L_i(f_{\theta_i'})$ associated with the N videos, determining adjustments to be made to the parameters θ based on a stochastic gradient descent (e.g., second-order derivatives) associated with the average loss, and backpropagating the adjustments through the image processing system based on the learning rate β, as illustrated below:

$$\theta \leftarrow \theta - \beta \nabla_\theta \frac{1}{N} \sum_{i=1}^{N} L_i(f_{\theta_i'}) \quad (4)$$

Figure 5:
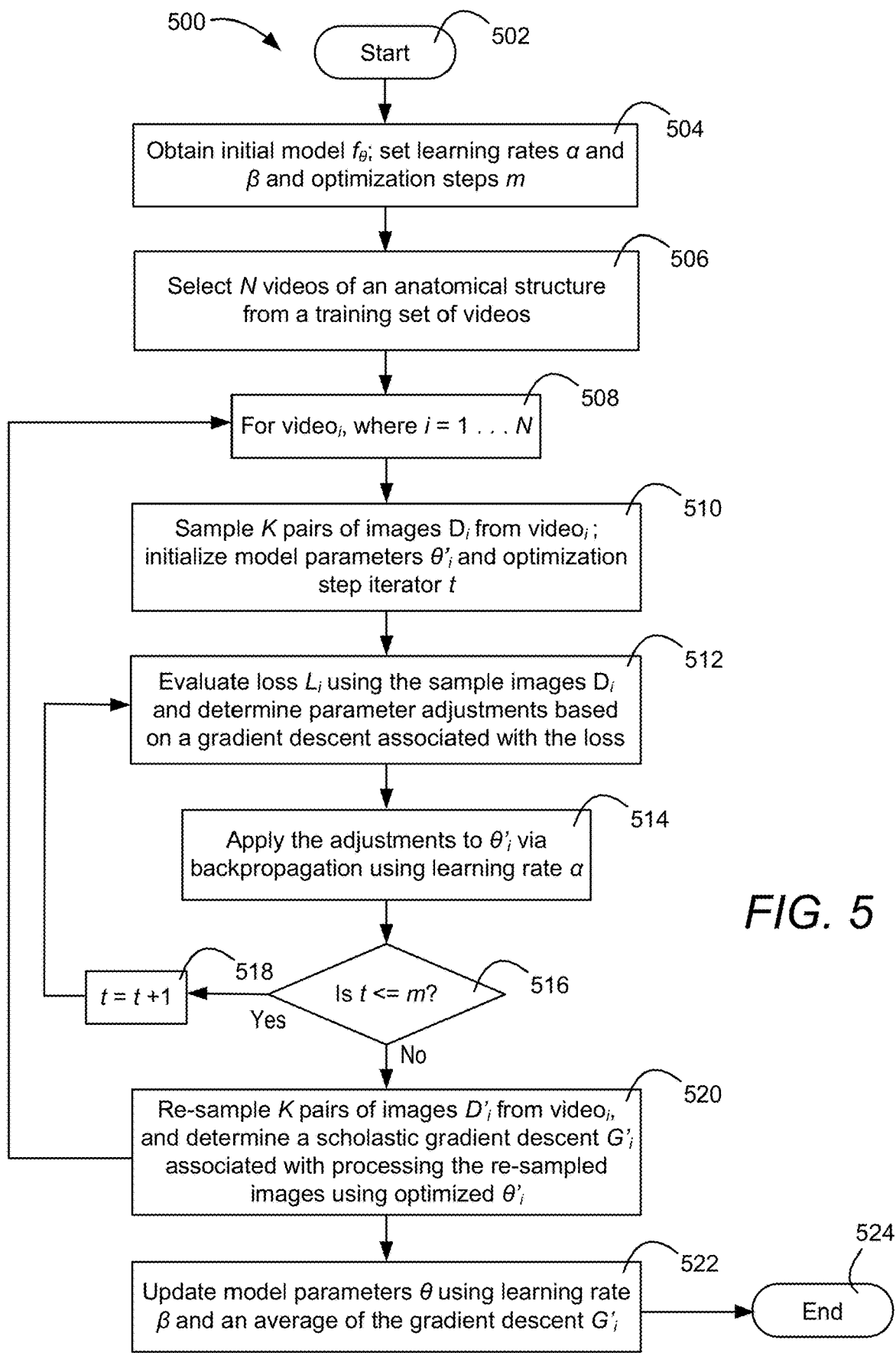
FIG. 5 is another flow diagram illustrating an example of meta-learning in accordance with one or more embodiments described herein.

Through the meta-learning process described herein, the image processing system may acquire high-quality initial model parameters that allow for fast and flexible adaptation of the model parameters based on real medical imaging data once the image processing system is brought online and provided with samples of the real data for optimization. It should be noted that the online optimization and meta-learning techniques described herein may be generally applicable to many types of applications and may not require the specific neural network structures, processes or algorithms disclosed with the examples. For instance, the meta-learning process illustrated in FIG. 4 may be modified (e.g., as shown in FIG. 5) such that, after the inner for-loop, the image processing system may determine a stochastic gradient descent $G_i$ for each of the N videos based on a loss associated with processing the re-sampled K pairs of images D using a respective optimized copy of the network parameters, $\theta_i'$, and subsequently (e.g., after the outer for-loop) adjust the predetermined parameter θ by calculating an average of the respective gradient descents $G_i$ (e.g., a second-order derivative) associated with the N videos, determining adjustments to be made to the parameters θ based on the average gradient descent, and backpropagating the adjustments through the image processing system based on the learning rate β, as illustrated below and illustrated by 520-522 of FIG. 5.

$$\theta \leftarrow \theta - \beta \frac{1}{N} \sum_{i=1}^{N} \nabla_\theta L_i(f_{\theta_i'}) \quad (5)$$

The modification described above may improve the efficiency of calculation and/or graphics processing unit GPU memory usage. For instance, the image processing tasks described herein may involve storing a larger number of feature maps (e.g., given a larger image size of 192×192) and as such may require a large amount of GPU memory. By swapping the gradient operator and the average operator as shown in Equations (4) and (5), the gradients may be computed on one or more GPUs before being transferred to a CPU. As another example of modifications, instead of using second-order derivatives that may involve calculating a second-order Hessian matrix during the backpropagation (e.g., as shown in Equations (4) and (5)), first-order approximation may be applied to reduce the computation costs of the meta-learning.

Figure 6:
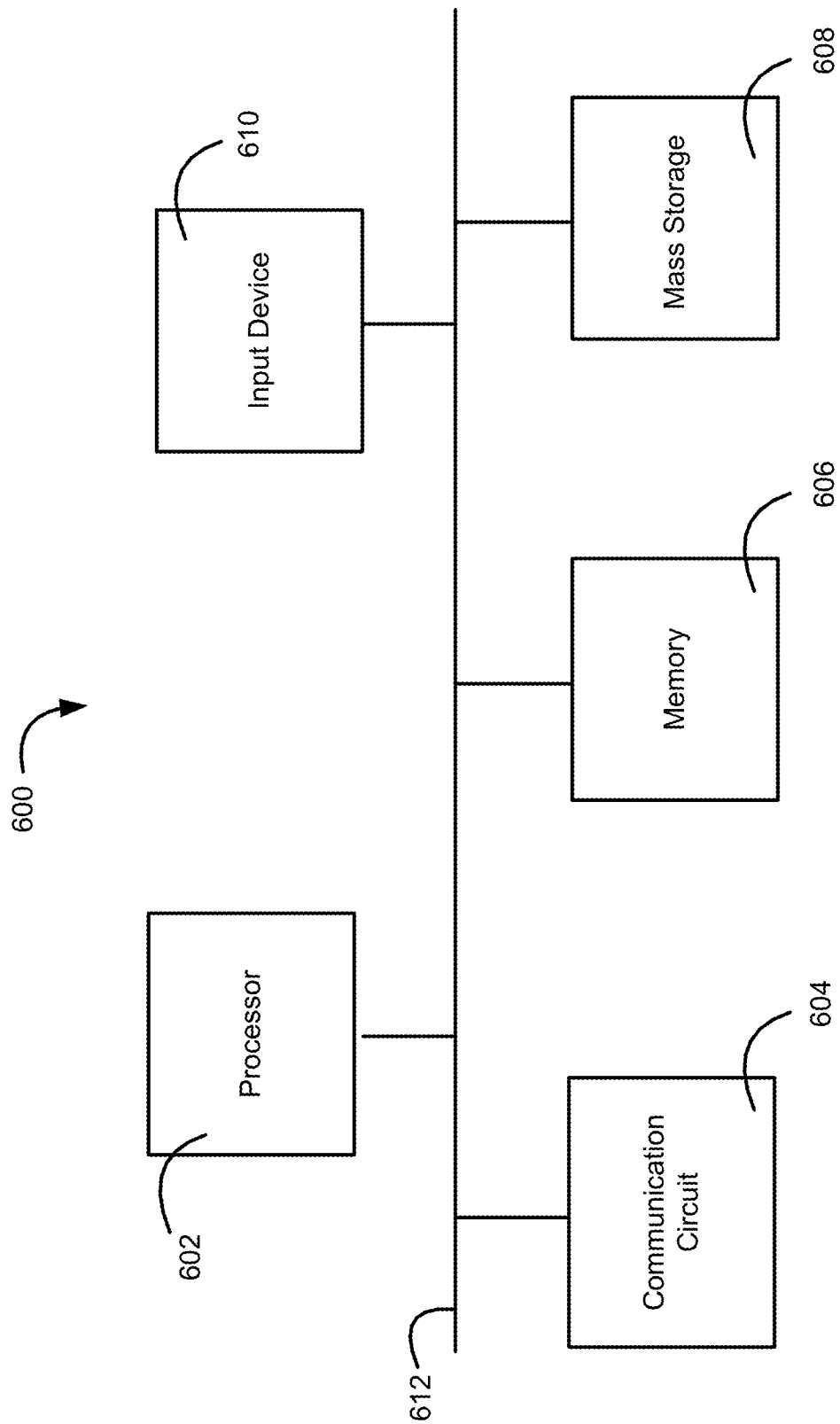
FIG. 6 is a block diagram illustrating example components of the image processing system described herein.

The image processing system described herein (e.g., such as the system 200 in FIG. 2) may be implemented using one or more processors, one or more storage devices, and/or other suitable accessory devices such as display devices, communication devices, input/output devices, etc. FIG. 6 is a block diagram illustrating an example image processing system 600 as described herein. As shown, the image processing system 600 may include a processor (e.g., one or more processors) 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The image processing system 600 may further include a communication circuit 604, a memory 606, a mass storage device 608, an input device 610, and/or a communication link 612 (e.g., a communication bus) over which the one or more components shown in FIG. 6 may exchange information. The communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 606 may include a storage medium configured to store machine-readable instructions that, when executed, cause the processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 602. The input device 610 may include a keyboard, a mouse, a voice-controlled input device, a touch sensitive input device (e.g., a touch screen), and/or the like for receiving user inputs to the image processing system 600.

It should be noted that the image processing system 600 may operate as a standalone device or may be connected (e.g., networked or clustered) with other computation devices to perform the functions described herein. And even though only one instance of each component is shown in FIG. 6, a skilled person in the art will understand that the image processing system 600 may include multiple instances of one or more of the components shown in the figure. Furthermore, although the examples are described herein with reference to various types of neural networks, various types of layers, and/or various tasks being performed by certain types of neural networks or layers, those references are made merely for illustration purposes and not meant to limit the scope of the disclosure. In addition, the operation of the example image processing system is depicted and described herein with a specific order. It should be appreciated, however, that these operations may occur in various orders, concurrently, and/or with other operations not presented or described herein. And not all operations that the image processing system is capable of performing are depicted and described herein, and not all illustrated operations are required to be performed by the system.

Figure 7:
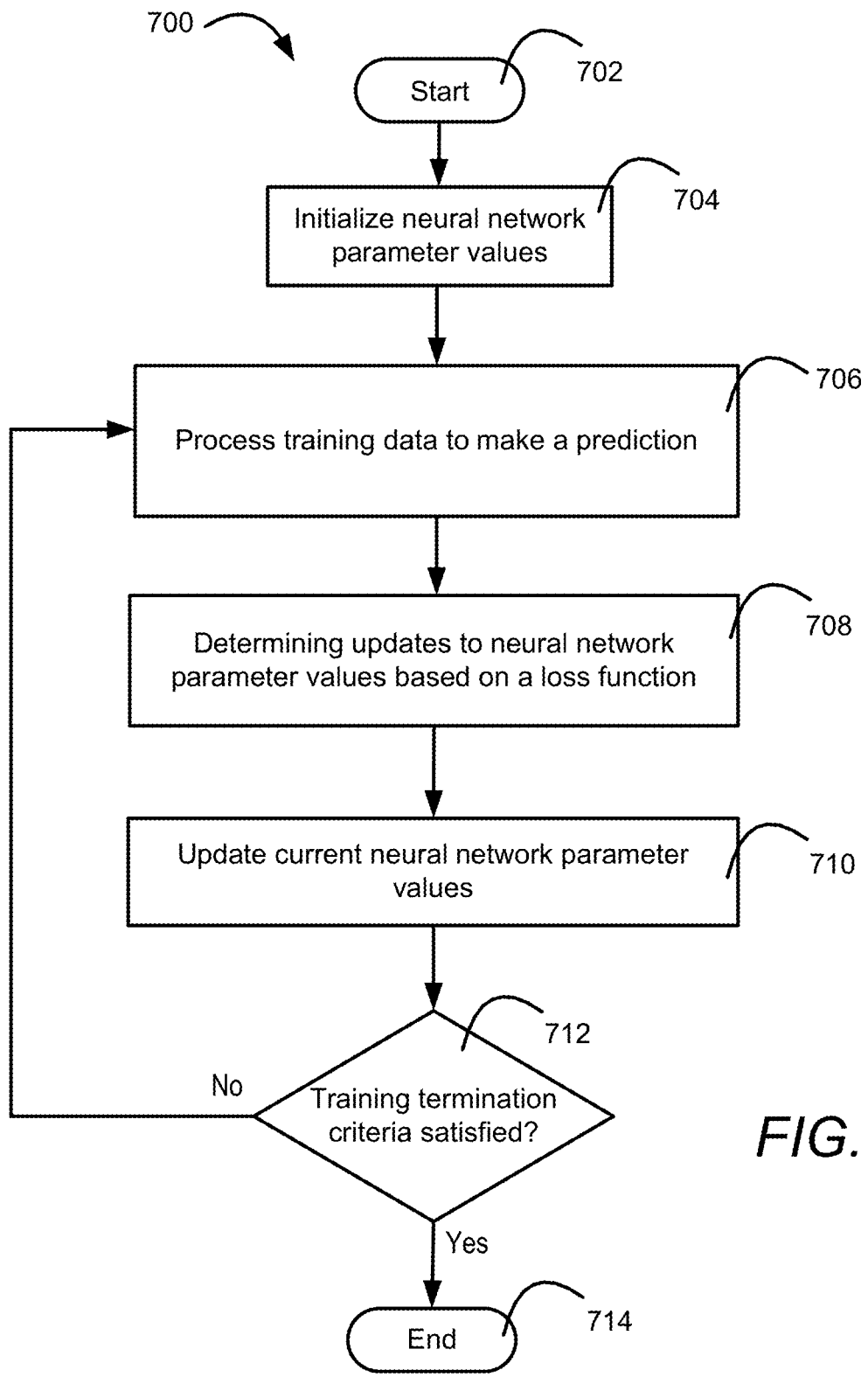
FIG. 7 is a flow diagram illustrating an example neural network training process in accordance with one or more embodiments described herein.

FIG. 7 is a flow diagram of an example process 700 for training a neural network (e.g., the feature tracking network 202 or motion tracking network 206 of FIG. 2). The process 700 may start at 702 and, at 704, the neural network may initialize its operating parameters such as the weights associated with one or more filters or kernels of the neural network. The parameters may be initialized, for example, based on samples from one or more probability distributions or parameter values of another neural network with a similar architecture. At 706, the neural network may receive one or more training images, process the images through the various layers of the neural network, and make a prediction for a target result (e.g., a motion field, a classification map, etc.) using presently assigned parameters. At 708, the neural network may determine adjustments to be made to the presently assigned parameters based on a loss function and a gradient descent (e.g., a stochastic gradient decent) associated with the loss function. For example, the loss function may be implemented based on a mean squared error (MSE) or an L1 norm distance between the prediction and a ground truth associated with the prediction. At 710, the neural network may carry out the adjustments to the presently assigned parameters, for example, via a backpropagation process. At 712, the neural network may determine whether one or more training termination criteria are satisfied. For example, the neural network may determine that the training termination criteria are satisfied if the neural network has completed a pre-determined number of training iterations, if the difference between the predicted values and the ground truth values is below a predetermined threshold, or if the change in the value of the loss function between two training iterations falls below a predetermined threshold. If the determination at 712 is that the training termination criteria are not satisfied, the neural network may return to 706. If the determination at 712 is that the training termination criteria are satisfied, the neural network may end the training process 700 at 714.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A system comprising at least one processor, wherein the at least one processor is configured to:
implement one or more artificial neural networks, wherein the one or more artificial neural networks are configured with a plurality of predetermined parameters for processing images of an anatomical structure;
bring the one or more artificial neural networks online to process the images; and
while the one or more artificial neural networks are online:
perform online adjustments to the plurality of predetermined parameters of the one or more artificial neural networks based on a first set of online images of the anatomical structure, wherein the online adjustments are performed by at least determining a loss associated with processing the first set of online images using the plurality of predetermined parameters and adjusting the plurality of predetermined parameters based on a gradient descent associated with the loss, and wherein the plurality of predetermined parameters are acquired via offline meta-learning that facilitates the online adjustments; and
process a second set of online images of the anatomical structure using the adjusted plurality of predetermined parameters of the one or more artificial neural networks.

2. The system of claim 1, wherein the online adjustments to the plurality of predetermined parameters are performed by backpropagating the gradient descent through the one or more artificial neural networks.

3. The system of claim 1, wherein the meta-learning is performed using multiple training videos of the anatomical structure, the meta-learning comprising:
obtaining baseline parameters for processing the images of the anatomical structure;
optimizing a respective copy of the baseline parameters based on a respective first loss associated with processing each of the multiple training videos using the respective copy of the baseline parameters;
determining a respective second loss associated with processing each of the multiple training videos using the respective optimized copy of the baseline parameters; and
updating the baseline parameters based on the respective second losses associated with the multiple training videos.

4. The system of claim 3, wherein the meta-learning comprises:
for each of the multiple training videos:
deriving the respective copy of the baseline parameters for the training video;
selecting a first set of training images from the training video;
determining a first loss associated with processing the first set of training images using the respective copy of the baseline parameters;
optimizing the respective copy of the baseline parameters based on a gradient descent associated with the first loss;
selecting a second set of training images from the training video; and
determining a second loss associated with processing the second set of training images using the respective optimized copy of the baseline parameters;
determining an average of the respective second losses associated with processing the respective second sets of training images of the multiple training videos; and
updating the baseline parameters based on a gradient descent associated with the determined average of the respective second losses.

5. The system of claim 4, wherein the respective first and second losses are determined based on a loss function and wherein the baseline parameters are updated based on a first order approximation of the loss function.

6. The system of claim 3, wherein the meta-learning comprises:
for each of the multiple training videos:
deriving the respective copy of the baseline parameters for the training video;
selecting a first set of training images from the training video;
determining a first loss associated with processing the first set of training images using the respective copy of the baseline parameters;
optimizing the respective copy of the baseline parameters based on a gradient descent associated with the first loss;
selecting a second set of training images from the training video; and
determining a second loss associated with processing the second set of training images using the respective optimized copy of the baseline parameters and a gradient descent associated with the second loss;
determining an average of the respective gradient descents associated with processing the respective second sets of training images of the multiple training videos; and
updating the baseline parameters based on the determined average of the respective gradient descents.

7. The system of claim 3, wherein the baseline parameters are derived based on a first training set characterized by a first distribution and wherein the multiple training videos are derived from a second training set characterized by a second distribution that mismatches the first distribution.

8. The system of claim 1, wherein the at least one processor being configured to process the images of the anatomical structure comprises the at least one processor being configured to track a motion of the anatomical structure based on the images or perform an image registration based on the images.

9. The system of claim 8, wherein the anatomical structure comprises a myocardium and the images are derived from a cardiac magnetic resonance (CMR) video.

10. The system of claim 1, wherein the one or more artificial neural networks comprise an encoder network and a decoder network.

11. A method implemented via at least one processor, the method comprising:
bringing one or more artificial neural networks online to process images of an anatomical structure, wherein the one or more artificial neural networks are configured with a plurality of predetermined parameters for processing the images of the anatomical structure; and
while the one or more artificial neural networks are online:
performing online adjustments to the plurality of predetermined parameters of the one or more artificial neural networks based on a first set of online images of the anatomical structure, wherein the online adjustments are performed by at least determining a loss associated with processing the first set of online images using the plurality of predetermined parameters and adjusting the plurality of predetermined parameters based on a gradient descent associated with the loss, and wherein the plurality of predetermined parameters are acquired via offline meta-learning that facilitates the online adjustments; and
processing a second set of online images of the anatomical structure using the adjusted plurality of predetermined parameters of the one or more artificial neural networks.

12. The method of claim 11, wherein performing the online adjustments to the plurality of predetermined parameters of the one or more artificial neural networks comprises backpropagating the gradient descent through the one or more artificial neural networks.

13. The method of claim 11, wherein the meta-learning is performed using multiple training videos of the anatomical structure, the meta-learning comprising:
obtaining baseline parameters for processing the images of the anatomical structure;
optimizing a respective copy of the baseline parameters based on a respective first loss associated with processing each of the multiple training videos using the respective copy of the baseline parameters;
determining a respective second loss associated with processing each of the multiple training videos using the respective optimized copy of the baseline parameters; and
updating the baseline parameters based on the respective second losses associated with the multiple training videos.

14. The method of claim 13, wherein the meta-learning comprises:
for each of the multiple training videos:
deriving the respective copy of the baseline parameters for the training video;
selecting a first set of training images from the training video;
determining a first loss associated with processing the first set of training images using the respective copy of the baseline parameters;
optimizing the respective copy of the baseline parameters based on a gradient descent associated with the first loss;
selecting a second set of training images from the training video; and
determining a second loss associated with processing the second set of training images using the respective optimized copy of the baseline parameters;
determining an average of the respective second losses associated with processing the respective second sets of training images of the multiple training videos; and
updating the baseline parameters based on a gradient descent associated with the determined average of the respective second losses.

15. The method of claim 14, wherein the respective first and second losses are determined based on a loss function and wherein the baseline parameters are updated based on a first order approximation of the loss function.

16. The method of claim 13, wherein the meta-learning comprises:
for each of the multiple training videos:
deriving the respective copy of the baseline parameters for the training video;
selecting a first set of training images from the training video;
determining a first loss associated with processing the first set of training images using the respective copy of the baseline parameters;
optimizing the respective copy of the baseline parameters based on a gradient descent associated with the first loss;

selecting a second set of training images from the training video; and determining a second loss associated with processing the second set of training images using the respective optimized copy of the baseline parameters and a gradient descent associated with the second loss;

determining an average of the respective gradient descents associated with processing the respective second sets of training images of the multiple training videos; and updating the baseline parameters based on the determined average of the respective gradient descents.

17. The method of claim 13, wherein the baseline parameters are derived based on a first training set characterized by a first distribution and wherein the multiple training videos are derived from a second training set characterized by a second distribution that mismatches the first distribution.

18. The method of claim 11, wherein processing the images of the anatomical structure comprises tracking a motion of the anatomical structure based on the images or performing an image registration based on the images.

19. The method of claim 18, wherein the anatomical structure comprises a myocardium and the images are derived from a cardiac magnetic resonance (CMR) video.

20. The method of claim 11, wherein the one or more artificial neural networks comprise an encoder network and a decoder network.

* * * * *